United States Patent [19]

Johnson et al.

[11] Patent Number: 4,881,526

[45] Date of Patent: Nov. 21, 1989

[54] INTRAVAGINAL ELECTRODE AND STIMULATION SYSTEM FOR CONTROLLING FEMALE URINARY INCONTINENCE

[75] Inventors: Michael T. V. Johnson, Minneapolis; Donald D. Maurer, Anoka, both of Minn.

[73] Assignee: Empi, Inc., St. Paul, Minn.

[21] Appl. No.: 200,037

[22] Filed: May 27, 1988

[51] Int. Cl.$^4$ ........................ A61H 21/00; A61N 1/05; A61N 1/36

[52] U.S. Cl. .................................. 128/24.5; 128/788; 128/421

[58] Field of Search ........... 128/788, 421, 422, 423 R, 128/24.1, 24.2, 24.5, 48, 49

[56] References Cited

U.S. PATENT DOCUMENTS

| | | | |
|---|---|---|---|
| 1,032,840 | 7/1912 | Keough | 128/788 X |
| 3,080,865 | 3/1963 | Vincent | 128/98 |
| 3,403,684 | 10/1968 | Stiebel et al. | 128/788 |
| 3,528,423 | 9/1970 | Lee | 128/295 |
| 3,554,184 | 1/1971 | Habib | 128/1 |
| 3,646,616 | 3/1972 | Keshin | 3/1 |
| 3,661,155 | 5/1972 | Lindan | 128/295 |
| 3,705,575 | 12/1972 | Edwards | 128/1 |
| 3,744,063 | 7/1973 | McWhorter et al. | 3/1 |
| 3,749,100 | 7/1973 | Von Der Mosel | 128/788 |
| 3,800,800 | 4/1974 | Garbe et al. | 128/408 |
| 3,866,613 | 2/1975 | Kenny et al. | 128/408 |
| 3,870,051 | 3/1975 | Brindley | 128/422 |
| 3,926,178 | 12/1975 | Feldzamen | 128/2 |
| 3,933,147 | 1/1976 | Du Vail et al. | 128/2 |
| 3,973,571 | 8/1976 | Suhel | 128/408 |
| 4,019,498 | 4/1977 | Hawtrey et al. | 128/1 R |
| 4,106,511 | 8/1978 | Erlandsson | 123/407 |
| 4,139,006 | 2/1979 | Corey | 128/127 |
| 4,153,059 | 5/1979 | Fravel et al. | 128/622 |

(List continued on next page.)

FOREIGN PATENT DOCUMENTS

| | | |
|---|---|---|
| 0101595 | 2/1984 | European Pat. Off. |
| 0178514 | 4/1986 | European Pat. Off. .......... 128/788 |
| 2502620 | 7/1975 | Fed. Rep. of Germany ...... 128/788 |
| 2822616 | 11/1979 | Fed. Rep. of Germany ...... 128/788 |
| 2261737 | 9/1975 | France ................................. 128/788 |
| 2547203 | 12/1984 | France . |
| 1145749 | 3/1969 | United Kingdom ............... 128/788 |

OTHER PUBLICATIONS

Hopkinson et al., "Electrical Treatment of Incontinence", Brit. J. Surg., 1967, pp. 802-804.

Rajaratnam, "Electrical Stimulation for the Control of Micuturition", New Zealand Medical Journal, Jun. 9, 1982, pp. 390-391.

Sotiropoulos et al., "Managment of Urinary Incontinence with Electronic Stimulation; Observations and Results", The Journal of Urology, 1976, pp. 747-750.

(List continued on next page.)

Primary Examiner—Lee S. Cohen
Attorney, Agent, or Firm—Kinney & Lange

[57] ABSTRACT

An intravaginal electrode and controller for preventing female urinary incontinence. The electrode includes an elongated and generally cylindrical carrier having a rounded tip, an extended lip, and a neck of reduced diameter located approximately eight centimeters from the lip. A pair of annular motor electrodes are positioned on an exterior surface of the carrier at longitudinally spaced locations on opposite sides of the neck. Sensory electrodes and an oscillatory transducer are mounted to the carrier adjacent the lip. Motor receptor electrical stimulation signals received from the controller are coupled to the motor electrodes and directly stimulate pelvic floor musculature. Sensory receptor electrical stimulation signals are coupled to sensory receptors through the sensory electrodes while tactile receptors are stimulated by mechanical oscillations from the oscillatory transducer. Stimulation of sensory and tactile receptors cause the central nervous system to contract the pelvic floor musculature and inhibit bladder wall muscle contraction. These stimulus combine for maximal activation of neural pathways.

29 Claims, 4 Drawing Sheets

U.S. PATENT DOCUMENTS

| | | | |
|---|---|---|---|
| 4,290,420 | 9/1981 | Manetta | 128/1 R |
| 4,296,760 | 10/1981 | Carlsson et al. | 128/788 |
| 4,349,031 | 9/1982 | Perlin | 128/642 |
| 4,387,719 | 6/1983 | Plevnik et al. | 128/421 |
| 4,406,288 | 9/1983 | Horwinski et al. | 128/422 |
| 4,431,001 | 2/1984 | Hakansson et al. | 128/421 |
| 4,457,299 | 7/1984 | Cornwell | 128/1 R |
| 4,515,167 | 5/1985 | Hochman | 128/736 |
| 4,542,753 | 9/1985 | Brenman et al. | 128/788 |
| 4,568,339 | 2/1986 | Steer | 604/329 |
| 4,580,578 | 4/1986 | Barsom | 128/784 |
| 4,688,575 | 8/1987 | DuVall | 128/422 |
| 4,785,828 | 11/1988 | Maurer | |

OTHER PUBLICATIONS

Bergmann et al., article entitled "Electrosstimulation in Urinary Incontinence" Book Title Unknown, Published by Karger AG Basel 1986, pp. 411–417.

Sotiropoulos, "Urinary Incontinence", *Urology*, Sep. 1975, pp. 312–381.

Merrill et al., "Urinary Incontinence Treatment with Electrical Stimulation of the Pelvic Floor", *Urology*, Jan. 1975, pp. 67–72.

Doyle, et al., "Treatment of Urinary Incontinence by External Stimulating Devices", *Urology International*, 1974, pp. 450–457.

Hopkinson, "The Birmingham Continence Aid", *Urology International*, 1974, pp. 211–212.

Erlandson, "Intravaginal Electrical Stimulation:Clinical Experiments on Urethral Closure", *Scand. J. Urol. Nephrol. Suppl.*, Part III, 1978, pp. 31–39.

Fall et al., "Contelle; Pelvic Floor Stimulation for Female Stress-Urge Incontinence A Multicenter Study", *Urology*, Mar. 1986, pp. 282–287.

Ormed Limited, brochure entitled "Conmax Short-Term Electrical Therapeutic Stimulation for Long-Term Improvement of Incontinence", undated, 4 pages.

Information Sheet Entitled "Georenje" Pertaining to Vagicon X Automatic Vaginal Stimulator, author unknown, undated.

Bradley et al., "Sphincter Electromyography", *Urologic Clincs of North America* Feb. 1974, 7 pages.

Rottembourg, "Study of the Efficiency of Electric Stimulation of the Pelvic floor", *Investigative Urology*, 1976, pp. 354–358.

Rockswold et al., "Electrophysiological Technique for Evaluating Lesions of the conus Meddullaris and Cauda Equina", *J. Neurosurg.*, Sept. 1976, pp. 321–325.

Harrison et al., "Female Urinary Incontinence", *Br. Med. J.*, 1969, pp. 619–620.

Brindley et al., "The Pressure Exerted by the External Sphincter of the Urehra when its Motor Nerve Fibers are Stimulated Electrically", *British Journal of Urology*, 1974, pp. 453–462.

Fall et al., "Electrical Stimulation in Interstitial Cystitis", *The Journal of Urology*, 1980, pp. 192–195.

Teague et al., "Electric Pelvic Floor Stimulation Mechanism of Action", *Investigative Urology*, 1977, pp. 65–69.

INTRAVAGINAL ELECTRODE AND STIMULATION SYSTEM FOR CONTROLLING FEMALE URINARY INCONTINENCE

BACKGROUND OF THE INVENTION

1. Field of the Invention.

The present invention relates generally to apparatus for intravaginal stimulation for use in the therapy of female urinary incontinence.

2. Description of the Prior Art.

The obstruction of urinary flow in females is managed by various contractive maneuvers of both involuntary smooth muscle and voluntary striated muscle. The first point of resistance is supplied by the so-called internal urethral sphincter. This sphincter is physiologic and consists of a continuation of smooth muscle from the bladder wall. Active contraction of the bladder causes a longitudinal contraction of this muscular layer, thereby shortening the urethral length and widening the urethral lumen. This action constitutes a relaxation of the sphincter. Sympathetic tone inhibits this opening of the internal urethral sphincter. Resistance to urine flow is also to some extent modulated by the tone of the urethral smooth muscle. Contraction decreases the lumenal diameter. This is also mediated by the sympathetic nervous system.

A second point of resistance to the flow of urine is the contracted external urethral sphincter. The external urethral sphincter consists of a circumferental cord of striated muscle and is innervated by the voluntary nervous system via the pudendal nerve. The autonomic reflex pattern, causing bladder emptying, can be inhibited by volitional contraction of the external urethral sphincter.

Alteration of the geometry of the pelvic floor also increases resistance to urine flow. The pelvic floor is created by a sling of striated muscle attached to the pelvic ring. These muscles, like the external urethral sphincter, are under voluntary control. The constituents of the pelvic floor musculature are the deep transverse perineal muscle and the levator ani (pubococcygeus, iliococcygeus) muscles blending with the external anal sphincter. Innervation for all groups derives from the pudendal nerve. Contraction of the pelvic floor musculature elevates the bladder, stretches the urethra, and causes an acute angulation of the urethral-vesicular junction. These alterations in the geometery of the urethra further increase the resistance to the flow of urine.

Urinary incontinence, the inability to control the passage urine, is a relatively common problem in females. Although there are a variety of different types of urinary incontinence, stress incontinence and urge incontinence are the most common. These two forms of incontinence are oftentimes found to exist together, a condition characterized as mixed incontinence.

Stress incontinence is described by the patient as the unacceptable passage of urine under the stress of increased abdominal pressure. This increased pressure typically results from coughing, sneezing, and Valsalva. Stress incontinence is manifest urologically by normal cystometry, obtuse urethral vesicular angle, abnormally low urethral pressures and a physiologically short urethral length. This disorder is most common in multiparous, post-menopausal females. Physiologically, stress incontinence is a disorder of the volitional muscular control of the urethral resistance to the flow of urine. Laxity and partial denervation of the pelvic musculature is the chief abnormality.

Urge incontinence is described as the involuntary passage of urine with a concomittant sense of urgency. Systometry indicates detrusor (bladder wall muscle) contractions with low bladder filling pressures and volumes. These bladder contractions may not be inhibited in the presence of voluntary EMG signals from the sphincter, indicating reduction or loss of the pudendal-parasympathetic inhibitory reflex. Unsolicited, premature bladder contraction may result from mucosal irritation of varied etiology. These premature contractions of the bladder may also be the result of an abnormally high gain in the detruser contractile reflex due to the loss of inhibitory control with an upper-motor-neuron lesion.

Electrical stimulation delivered by an intravaginal or a perineal surface electrode has been shown to inhibit premature and inappropriate detruser contractions. The mechanism for this effect derives from the stimulation of pudendal nerve afferents (sensory receptors or sensory nerve fibers). Input into the pudendal afferent system inhibits a parasympathetic reflex loop consisting of bladder wall afferents (sensory) and efferents (motor). This parasympathetic loop normally senses a distension of the blader via the afferent limb and responds by sending an efferent signal to contract the bladder.

Stimulation of pudendal nerve afferents causes a reflexive contraction of the pelvic floor musculature, mediated by pudendal nerve efferents. In this respect, therapeutic stimulation for stress incontinence requires the same afferent input as that for urge incontinence. However, mobilization of the pelvic floor muscles requires a greater input than that required for bladder relaxation. It is known that the stimulation of the neighboring pelvic floor musculature, such as the deep transverse perineal and external urethral sphincteric muscles, and/or local efferent nerve input, will cause contractions which help prevent incontinence.

Vibratory or other tactile stimulus for stimulating sensory receptors is known generally in neurophysiology. By way of example, sexual aids sometimes include vibratory transducers. However, the use of tactile stimulus for controlling urinary incontinence is apparently undocumented.

It is evident that there is a continuing need for improved urinary incontinence stimulation systems. Although various physiological mechanisms for preventing incontinence are known, they are ineffectively utilized by known stimulation systems. A stimulation system which maximizes the direct motor neural input yet makes use of a variety of physiological sensory reflex mechanisms to prevent incontinence is desired. This system must also be convenient and comfortable to use, to ensure patient acceptance.

SUMMARY OF THE INVENTION

An intravaginal electrode assembly in accordance with the present invention includes an elongated and generally cylindrical carrier having a tip at a distal end and an extended lip at a proximal end. A pair of motor electrodes are positioned adjacent one another on an exterior surface of the elongated carrier approximately eight centimeters from the lip. Sensory stimulation means are mounted to the carrier adjacent the lip. Motor electrode terminal means are coupled to the pair of motor electrodes and receive motor receptor electrical stimulation signals. Sensory receptor stimulation signals are coupled to the sensory stimulation means through sensory stimulation terminal means.

In one embodiment the carrier includes a neck of reduced diameter approximately eight centimeters from the lip. The motor electrodes are annular, extend around a circumference of the carrier, and are positioned at longitudinally spaced locations on opposite sides of the neck.

In another embodiment the sensory stimulation means include first and second sensory electrodes positioned on an exterior surface of the carrier with the first sensory electrode located adjacent the lip. The sensory stimulation terminal means is coupled to the sensory electrodes and receives sensory receptor electrical stimulation signals. The first sensory electrode has a greater surface area than the motor electrodes.

In another embodiment the sensory stimulation means includes an oscillatory transducer. The sensory stimulation terminal means is coupled to the oscillatory transducer and receives oscillatory transducer drive signals. The oscillatory transducer can be mounted within the carrier.

Still other embodiments include a controller which includes motor stimulation signal generation and control means and sensory stimulation signal generation and control means. The motor stimulation signal generation and control means is coupled to the motor electrode terminal means and produces the motor receptor electrical stimulation signals. The sensory stimulation signal generation and control means is coupled to the sensory stimulation terminal means and produces a sensory receptor stimulation signal. Motor/sensory phase control means coupled to the motor stimulation signal generation and control means and to the sensory stimulation signal generation and control means can also be included. The motor/sensory phase control means controls a phase relationship between the motor receptor stimulation signals and the sensory receptor stimulation signals.

DETAILED DESCRIPTION OF THE PREFERRED EMBODIMENTS

Figure 1:
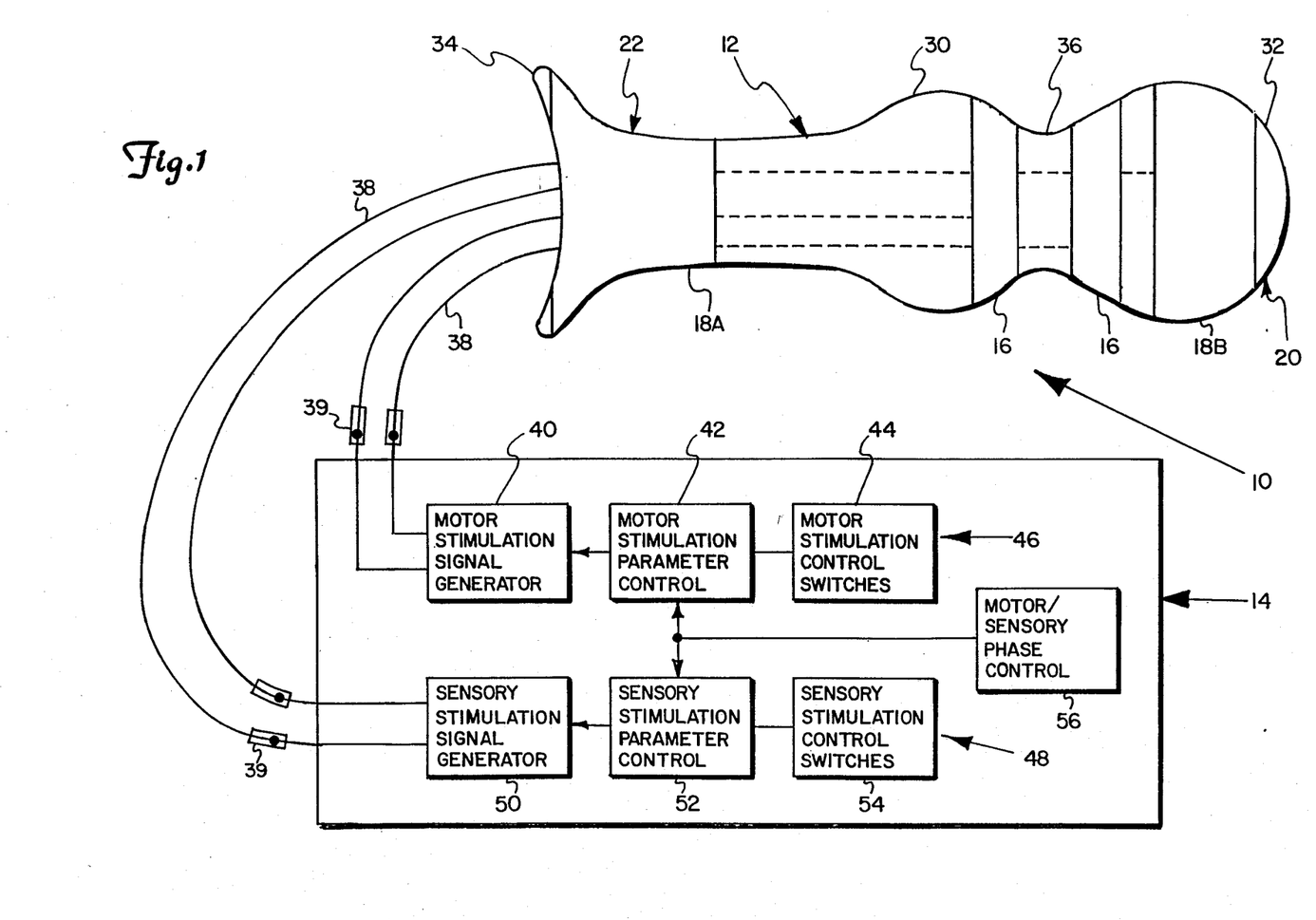
FIG. 1 is an illustration of an incontinence stimulation system in accordance with a first embodiment of the present invention.

A first embodiment of the present invention, female urinary incontinence stimulation system 10, is illustrated generally in FIG. 1. As shown, stimulation system 10 includes an intravaginal electrode assembly 12 and a controller 14. Electrode assembly 12 is formed by a body or carrier 30 having an exterior surface to which a pair of sensory electrodes 16 and a pair of motor electrodes 18A, 18B are mounted. Carrier 30 is an elongated and preferably cylindrical member having a distal end 20 and a proximal end 22. A conical or rounded tip 32 formed on distal end 20 of carrier 30 facilitates the placement of electrode assembly 12 within a woman's vagina. An extended lip 34 formed on proximal end 22 prevents deep migration of electrode assembly 12 into the vagina. A concave neck 36 having a reduced diameter from adjacent portions of carrier 30 is located between tip 32 and lip 34. As shown, neck 36 is positioned a distance D from lip 34. Distance D corresponds to the distance of lower pelvic musculature from the introitus or vaginal opening. In a typical adult female, distance D will be approximately eight centimeters. Distance D will of course vary with the anatomical structure of individual females, and is generally in a range of six to ten centimeters. Carrier 30 can be molded from polymer materials, although other suitable materials and fabrication methods can also be used. In other embodiments, carrier 30 is formed from resilient material at a location corresponding to neck 36.

Electrodes 16 and 18A, 18B can be fabricated from a variety of materials including metals, carbonized rubber, and conductive polymers. In the embodiment shown, electrodes 16 and 18A, 18B are annular or ring-shaped, and extend around the circumference of carrier 30. Electrodes 16 and 18A, 18B can be molded into the surface of carrier 30 during its fabrication, or fastened to its exterior surface by adhesives or other fabrication techniques. In one embodiment electrodes 16 and 18A, 18B are formed as integral members of a condom which is removably unrolled onto carrier 30. An electrode assembly having a condom of this type is disclosed in copending application Ser. No. 06/916,118, filed Oct. 6, 1986, now U.S. Pat. No. 4,785,828, entitled Vaginal Stimulator For Controlling Urinary Incontinence In Women, and assigned to the same assignee as that of the present invention.

In the embodiment shown in FIG. 1, motor electrodes 16 are positioned adjacent one another at longitudinally spaced locations on opposite sides of neck 36. Motor electrodes 16 are approximately three-eighths of an inch in width in one embodiment. Sensory electrode 18A is positioned adjacent proximal end 22 of carrier 30, and extends over much of the exterior surface of lip 34 in the embodiment shown. Sensory electrode 18A is relatively wide with respect to motor electrodes 16, and has a larger surface area. Sensory electrode 18A is on the order of one inch in width in one embodiment. In the embodiment shown, sensory electrode 18B is positioned on tip 32 of carrier 30, opposite motor electrodes 16 from sensory electrode 18A. Sensory electrode 18B is approximately three-fourths of an inch wide in one embodiment. Sensory electrodes 18A, 18B and motor electrodes 16 are each coupled to controller 14 by a lead 38 in the embodiment shown. Leads 38 extend into the interior of carrier 30 from its distal end 22 adjacent lip 34, and can be conveniently interconnected to controller 14 by means of plug terminals 39.

Controller 14 includes motor stimulation signal generation and control circuitry 46, sensory stimulation signal generation and control circuitry 48 and motor/sensory phase control 56. In the illustrated embodiment, motor stimulation signal circuitry 46 includes motor stimulation signal generator 40, motor stimulation parameter control circuitry 42, and motor stimulation control switches 44. Motor stimulation signal generator 40 produces stimulation signals in the form of a train of electrical pulses having characteristics which will directly induce contractions of the pelvic floor musculature when applied to the motor end plates of the musculature through motor electrodes 16. Parameters of the motor stimulation signals, including pulse amplitude, pulse width, pulse frequency and modulation mode are controlled by motor stimulation parameter control circuitry 42 in response to operator actuation of motor stimulation control switches 44. Circuitry for generating and modulating electrical stimulation signals is known and disclosed, for example, in application Ser. No. 06/757,705, filed July 22, 1985, entitled Medical Stimulator With Stimulation Signal Characteristics Modulated As A Function Of Stimulation Signal Frequency, and assigned to the same assignee as that of the present invention.

Sensory stimulation signal generation and control circuitry 48 includes sensory stimulation signal generator 50, sensory stimulation parameter control circuitry 52, and sensory stimulation control switches 54. Sensory stimulation signal generator 50 produces electrical stimulation signals in the form of pulses having characteristics which induce contractions of the pelvic musculature and relaxation of the bladder detrusor muscles in response to their application to cutaneous nerve receptors through sensory electrodes 18A and 18B. Parameters of the sensory stimulation signals produced by generator 50 are controlled by sensory stimulation parameter control 52 in response to operator actuation of sensory stimulation control switches 54. As shown, motor/sensory phase control 56 is coupled to motor stimulation parameter control 42 and sensory stimulation parameter control 52. In response to operator actuation, motor/sensory phase control 56 controls the phase between the modulation and/or other signal parameters of the motor and sensory stimulation signals. The relative phases of these signals can then be fixed in time or shifted in a periodic manner to help reduce accommodation and adaptation of the neural systems.

Figure 2:
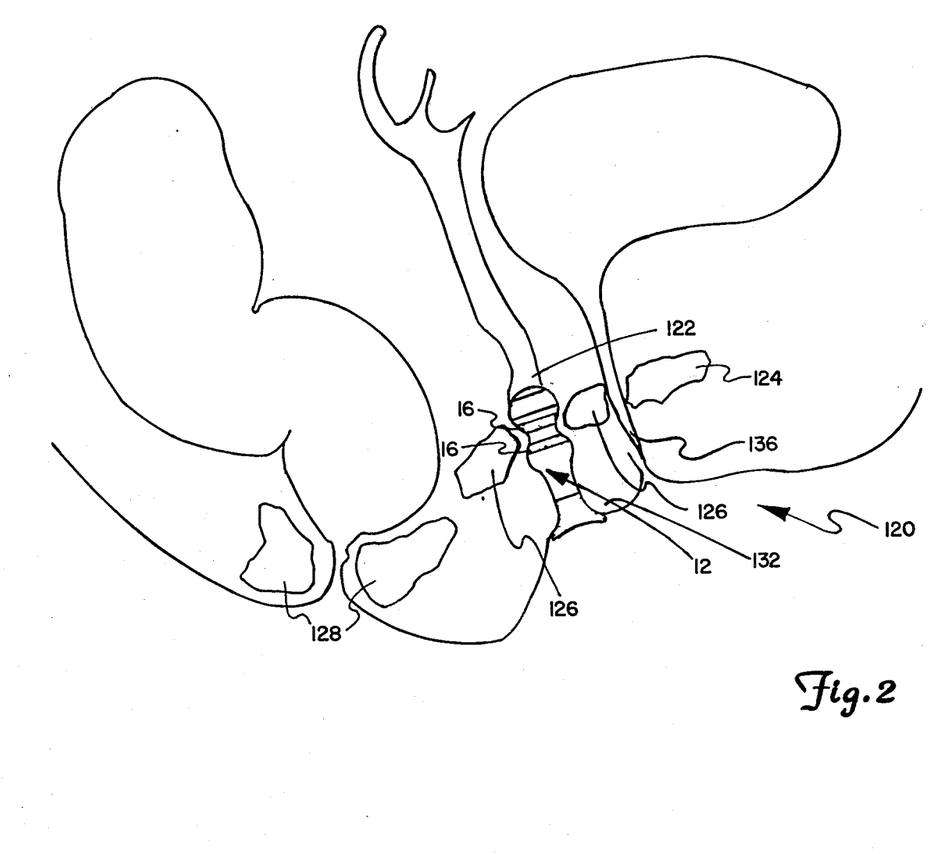
FIG. 2 is a sagittal cross-section of a female pelvic region illustrating the placement of the electrode assembly shown in FIG. 1.

FIG. 2 is a sagittal cross-section of a female pelvic region 120 illustrating the placement of electrode assembly 12 in vagina 122. Lip 34 stabilizes the external aspect of carrier 30 against an undergarment (not shown) of the patient. The precise longitudinal placement of electrodes 16 and 18A, 18B on carrier 30 ensures critical alignment with the appropriate anatomic structure for optimum motor and sensory stimulation.

Motor electrodes 16 will be accurately positioned adjacent the plane of the sheet of pelvic muscles where they cross the mucosa and smooth muscle cylinder of vagina 122. This sheet of muscles includes external urethral sphincteric muscle 124, deep transverse perineal muscle 126, and external rectal sphincter muscle 128. Since motor electrodes 16 are positioned adjacent perineal muscles 126, the motor end plates of these and other pelvic muscles will be directly stimulated by the motor stimulation signals. This direct stimulation will cause local contractions which stretch and constrict urethral canal 136. The contraction of the planar arrangement of sphincter muscle 124 and perineal muscle 126 will also fill neck 36, or compress the resilient material of carrier 30 at this location, and further stabilize the longitudinal position of electrode assembly 12 within vagina 122.

Lip 34 also causes sensory electrode 18A to be positioned adjacent introitus 132 of vagina 122, the location at which the density of cutaneous sensory or pudendal nerve afferent receptors is at its maximum. The application of sensory stimulation signals through electrodes 18A and 18B will therefore efficiently recruit a large population of these receptors. In response, the central nervous system will further contract muscles 124 and 126, and relax the detrusor muscle by inhibiting the parasympathetic reflex loop. This action helps prevent the passage of urine through urethra 136. Since sensory electrode 18A has a relatively large surface area (i.e. compared to motor electrodes 16), relatively low current densities can be used to effectively recruit the required number of receptors. Localized burns and irritation can therefore be kept to a minimum.

Figure 3:
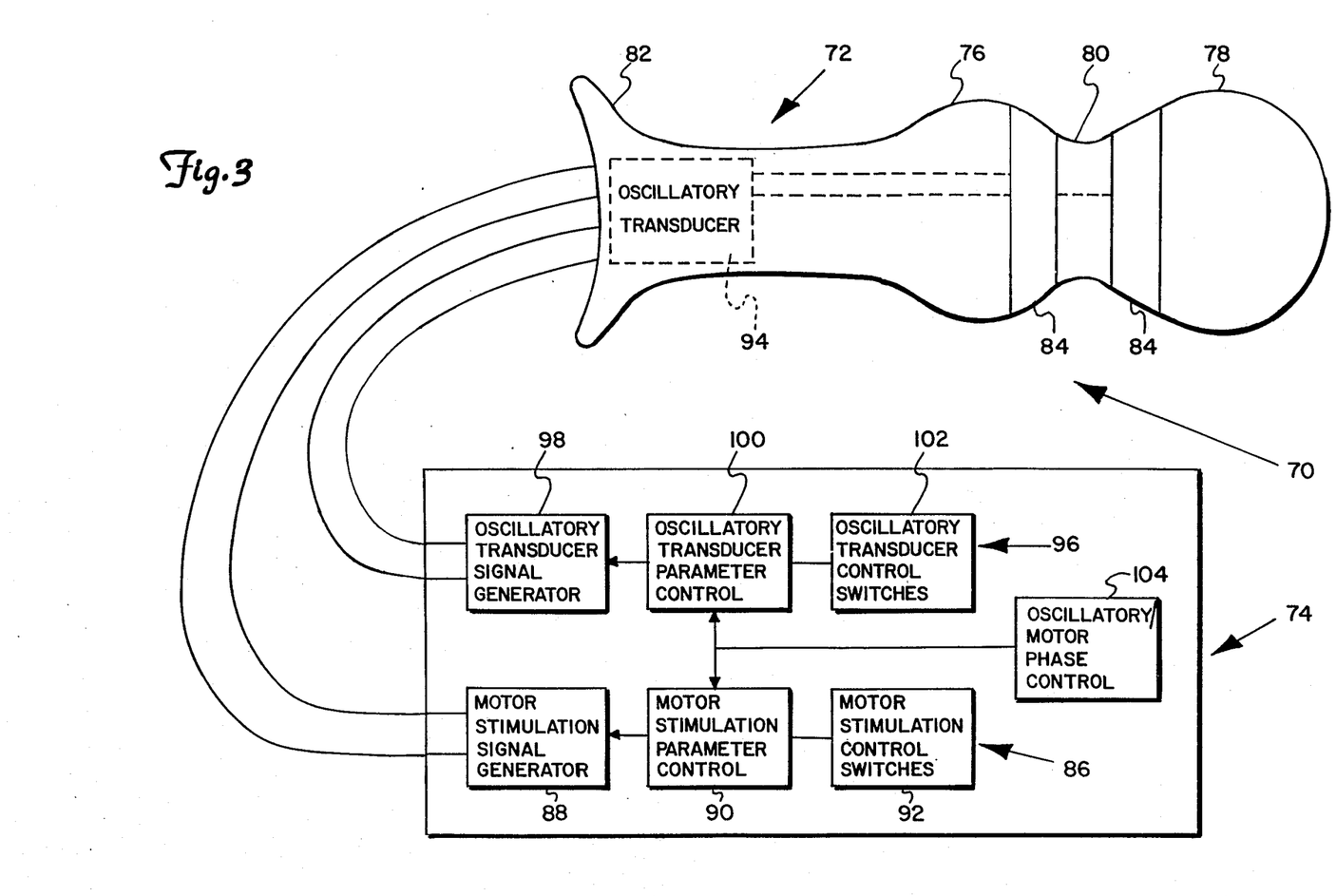
FIG. 3 is an illustration of an incontinence stimulation system in accordance with a second embodiment of the present invention.

Intravaginal stimulation system 70, a second embodiment of the present invention, is illustrated generally in FIG. 3. Stimulation system 70 includes an electrode assembly 72 and controller 74. Electrode assembly 72 includes a carrier 76 which has a rounded tip 78 on its distal end 79, an extended lip 82 on its proximal end 83, and a neck 80 between the lip and neck. A pair of motor electrodes 84 are positioned on opposite sides of neck 80. Carrier 76 and electrodes 84 can be identical to their counterparts in incontinence stimulation system 10 which was described above with reference to FIG. 1.

Motor stimulation signals are generated by motor stimulation signal generation and control circuitry 86, and applied to electrodes 84 through plug terminals 87 and leads 89. Motor stimulation signal circuitry 86 includes motor stimulation signal generator 88, motor stimulation parameter control 90, and motor stimulation control switches 92. Motor stimulation circuitry 86 can be identical to motor stimulation circuitry 46 described above with reference to controller 14 of stimulation system 10. Motor stimulation signals applied to the pelvic musculature when electrode assembly 72 is positioned within the vagina (in a manner similar to that of electrode assembly 12 shown in FIG. 2) will cause muscle contractions which help prevent the undesired flow of urine.

Electrode assembly 72 also includes sensory or tactile stimulation means such as oscillatory transducer 94 mounted in or on carrier 76 adjacent distal end 83 and lip 82. Oscillatory transducer 94 can be any of a wide variety of known devices including an off center motor driven cam, piezoelectric transducer, solenoid and spring, or magnetostriction device. Oscillatory transducer drive signals are produced by ocsillatory drive signal generation and control circuitry 96 which includes oscillatory transducer signal generator 98, oscillatory transducer parameter control circuitry 100 and oscillatory transducer control switches 102. Oscillatory drive signals having characteristics needed to drive transducer 94 are produced by signal generator 98. Characteristics of the transducer drive signals, and therefore the parameters of the oscillations produced by transducer 94 (e.g. amplitude and frequency) are controlled by parameter control circuitry 100 in response to operator actuation of control switches 102.

In one embodiment, circuitry 96 causes oscillatory transducer 94 to generate vibrations in the range of twenty to five hundred cycles per second. For power efficiency considerations, the stimulation can be in the form of short bursts of energy with large off to on cycles. These vibrations will also be coupled to electrodes 88 through carrier 76 to induce pressure or tactile sensory responses throughout the vagina. Phase or other relationships between the motor stimulation signals and oscillatory transducer drive signals are controlled by an operator through actuation of oscillatory/motor phase control 104.

The mechanical oscillations produced by oscillatory transducer 94 augment direct motor stimulation by activating touch or pressure responsive neuroreceptors such as Pacinian and Meissners corpuscles. Although these receptors are distributed throughout the vagina, their density is greatest adjacent introitus 132 (FIG. 2). The vibratory stimulation of these receptors causes the patient's central nervous system to relax the detrusor muscle while contracting the pelvic musculature. These actions augment the direct motor stimulation in the prevention of incontinence. In addition to maximizing neurophysiological input, difficulties encountered in the use of electrical stimulus alone can be overcome. Electrical stimulation around introitus 132 is often perceived as an irritating or painful sensation. Electrical stimulation at sufficient intensity to produce a reflex contraction can also cause local electrical burns. A combination of electrical and mechanical stimulation produced by incontinence stimulation system 70 reduces many of these problems while providing optimal safe stimulus with maximal activation of neural pathways.

Figure 4:
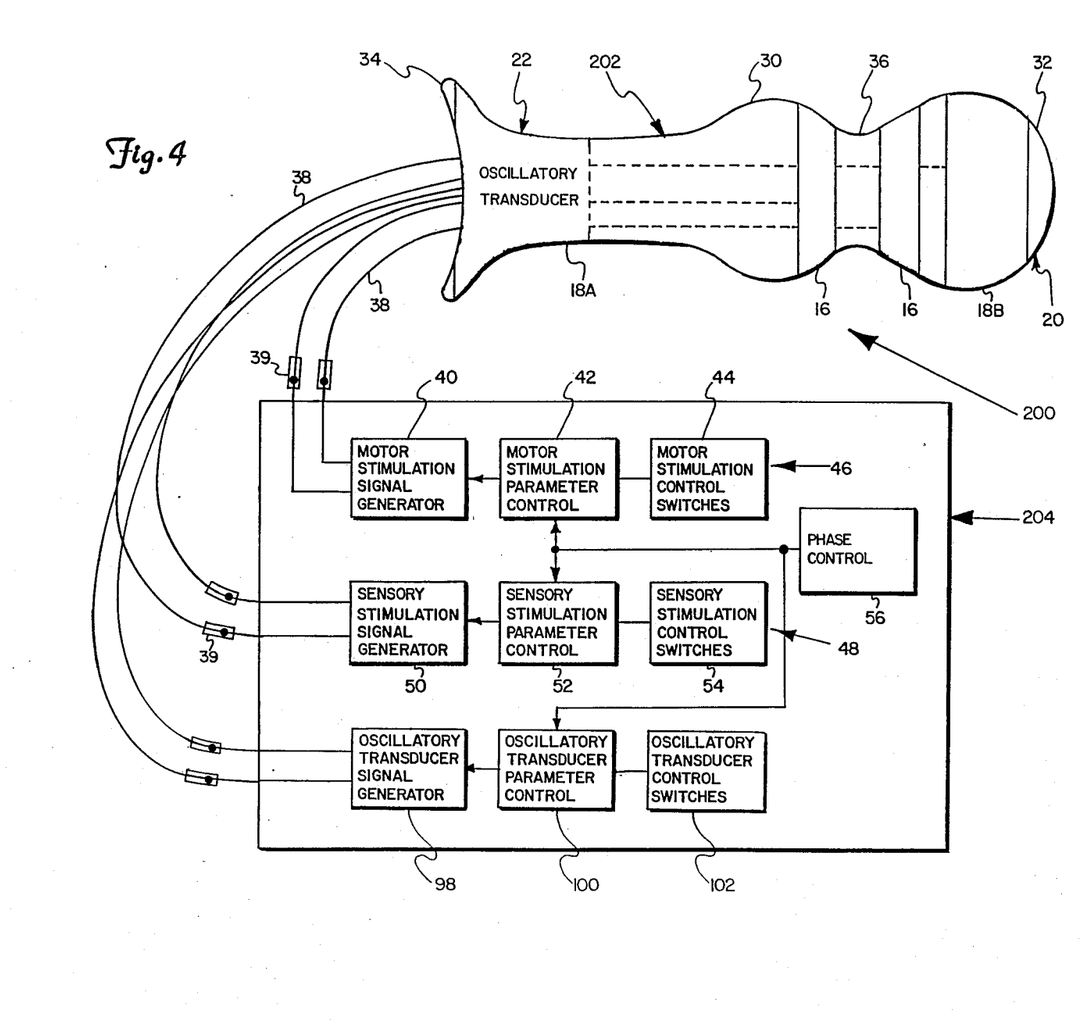
FIG. 4 is an illustration of an incontinence stimulation system in accordance with a third embodiment of the present invention.

Intravaginal stimulation system 200, a third embodiment of the invention, is illustrated generally in FIG. 4. Stimulation system 200 includes an electrode assembly 202 and controller 204. Electrode assembly 202 includes a carrier 30 which can be identical to that of stimulation system 10 described with reference to FIG. 1. As shown, electrode assembly 202 includes a pair of motor electrodes 16, a pair of sensory electrodes 18A and 18B, and an oscillatory transducer 94. Again, these components can be identical to their counterparts previously described with reference to stimulation systems 10 and 70.

Controller 204 includes motor stimulation signal generation and control circuitry 46, sensory stimulation signal generation and control circuitry 48, and oscillatory transducer drive signal generation and control circuitry 96. These elements can all function in a manner identical to their counterparts described above with reference to stimulation systems 10 and 70. Phase control 206 is interconnected to motor stimulation parameter control 42, sensory stimulation parameter control 52, and oscillatory transducer parameter control 100, and is actuated by an operator to control the relative phase of the various stimulus applied by means of electrode assembly 202. Stimulation system 200 maximizes both sensory and motor stimulus to help reduce urinary incontinence.

Although the present invention has been described with reference to preferred embodiments, workers skilled in the art will recognize that changes may be made in form and detail without departing from the spirit and scope of the invention.

What is claimed is:

1. An intravaginal electrode assembly including:
 an elongated and generally cylindrical carrier having a tip at a distal end and an extended lip at a proximal end;
 a pair of motor electrodes positioned adjacent one another on an exterior surface of the elongated carrier between the tip and lip approximately eight centimeters from the lip;
 sensory stimulation means for stimulating sensory receptors mounted to the carrier adjacent the lip;
 motor electrode terminal means coupled to the pair of motor electrodes, for receiving motor receptor electrical stimulation signals; and
 sensory stimulation terminal means coupled to the sensory stimulation means, for receiving sensory receptor stimulation signals.

2. The electrode assembly of claim 1 wherein the carrier includes means forming a neck of reduced diameter located between the tip and lip and approximately eight centimeters from the lip.

3. The electrode assembly of claim 2 wherein the motor electrodes are positioned on opposite sides of the means forming the neck.

4. The electrode assembly of claim 1 wherein the motor electrodes are annular, extend around a circumference of the carrier, and are positioned at longitudinally spaced locations on the carrier.

5. The electrode assembly of claim 1 wherein:
 the sensory stimulation means includes first and second sensory electrodes positioned on an exterior surface of the carrier with the first sensory electrode located adjacent the lip; and
 the sensory stimulation terminal means is coupled to the sensory electrodes and receives sensory receptor electrical stimulation signals.

6. The electrode assembly of claim 5 wherein the sensory electrodes are annular, extend around a circumference of the carrier, and are positioned at longitudinally spaced locations on the carrier.

7. The electrode assembly of claim 6 wherein the first sensory electrode has a greater surface area than the motor electrodes.

8. The electrode assembly of claim 5 wherein the second sensory electrode is positioned adjacent the distal end of the carrier.

9. The electrode assembly of claim 1 wherein:
 the sensory stimulation means includes an oscillatory transducer; and
 the sensory stimulation terminal means is coupled to the oscillatory transducer and receives oscillatory transducer drive signals.

10. The electrode assembly of claim 9 wherein the oscillatory transducer is mounted within the carrier.

11. The electrode assembly of claim 1 wherein:
 the sensory stimulation means includes:
  first and second sensory electrodes positioned on an exterior surface of the carrier with the first sensory electrode located adjacent the lip; and
  an oscillatory transducer; and
 the sensory stimulation terminal means includes:
  sensory electrode terminal means coupled to the sensory electrodes for receiving sensory receptor electrical stimulation signals; and
  oscillatory transducer terminal means coupled to the oscillatory transducer for receiving oscillatory transducer drive signals.

12. The invention of claim 11 and further including a controller comprising:
 motor stimulation signal generation and control means coupled to the motor electrode terminal means for producing the motor receptor electrical stimulation signals;
 sensory stimulation signal generation and control means coupled to the sensory stimulation terminal means for producing the sensory receptor stimulation signals; and
 oscillatory stimulation signal generation and control means coupled to the oscillatory transducer terminal means for producing the oscillatory transducer drive signals.

13. The invention of claim 1 and further including a controller comprising:
 motor stimulation signal generation and control means coupled to the motor electrode terminal means for producing the motor receptor electrical stimulation signals; and sensory stimulation signal generation and control means coupled to the sensory stimulation terminal means for producing the sensory receptor stimulation signals.

14. The invention of claim 13 wherein the controller further includes motor/sensory phase control means coupled to the motor stimulation signal generation and control means and to the sensory stimulation signal generation and control means, for controlling a phase relationship between the motor receptor stimulation signals and the sensory receptor stimulation signals.

15. An intravaginal electrode assembly including:
   an elongated and generally cylindrical carrier having a tip at a distal end, an extended lip at a proximal end, and means forming a neck of reduced diameter located approximately eight centimeters from the lip;
   a pair of annular motor electrodes extending around a circumference of the carrier and positioned at longitudinally spaced locations on opposite sides of the means forming the neck;
   first and second annular sensory electrodes extending around a circumference of the carrier with the first sensory electrode located adjacent the lip;
   motor electrode terminal means coupled to the pair of motor electrodes, for receiving motor receptor electrical stimulation signals; and
   sensory electrode terminal means coupled to the sensory electrodes, for receiving sensory receptor electrical stimulation signals.

16. The electrode assembly of claim 15 wherein the first sensory electrode has a greater surface area than the motor electrodes.

17. The electrode assembly of claim 15 wherein the second sensory electrode is positioned adjacent the distal end of the carrier.

18. The invention of claim 15 and further including a controller comprising:
   motor stimulation signal generation and control means coupled to the motor electrode terminal means for producing the motor receptor stimulation signals; and
   sensory stimulation signal generation and control means coupled to the sensory stimulation terminal means for producing the sensory receptor stimulation signals.

19. The invention of claim 18 wherein the controller further includes motor/sensory phase control means coupled to the motor stimulation signal generation and control means and to the sensory stimulation signal generation and control means, for controlling a phase relationship between the motor receptor stimulation signals and the sensory receptor stimulation signals.

20. An intravaginal electrode assembly including:
   an elongated and generally cylindrical carrier having a tip at a distal end, an extended lip at a proximal end, and means forming a neck of reduced diameter approximately eight centimeters from the lip;
   a pair of annular motor electrodes which extend around a circumference of the carrier and are positioned at longitudinally spaced locations on opposite sides of the means forming the neck;
   an oscillatory transducer mounted to the carrier adjacent the lip;
   motor electrode terminal means coupled to the pair of motor electrodes, for receiving motor receptor electrical stimulation signals; and
   oscillatory transducer terminal means coupled to the oscillatory transducer for receiving oscillatory transducer drive signals.

21. The electrode assembly of claim 20 wherein the oscillatory transducer is mounted within the carrier.

22. The invention of claim 20 and further including a controller comprising:
   motor stimulation signal generation and control means coupled to the motor electrode terminal means for producing the motor receptor electrical stimulation signals; and
   oscillatory drive signal generation and control means coupled to the oscillatory transducer terminal means for producing the oscillatory transducer drive signals.

23. The invention of claim 22 wherein the controller further includes motor/sensory phase control means coupled to the motor stimulation signal generation and control means and to the oscillatory drive signal generation and control means, for controlling a phase relationship between the motor receptor stimulation signals and the transducer drive signals.

24. An intravaginal electrode assembly including:
   an elongated and generally cylindrical carrier having a tip at a distal end, an extended lip at a proximal end, and means forming a neck of reduced diameter approximately eight centimeters from the lip;
   a pair of annular motor electrodes which extend around a circumference of the carrier and are positioned at longitudinally spaced locations on opposite sides of the means forming the neck;
   first and second annular sensory electrodes extending around a circumference of the carrier with the first sensory electrode located adjacent the lip;
   an oscillatory transducer mounted to the carrier adjacent the lip;
   motor electrode terminal means coupled to the pair of motor electrodes, for receiving motor receptor electrical stimulation signals;
   sensory electrode terminal means coupled to the sensory electrodes, for receiving sensory receptor electrical stimulation signals; and
   oscillatory transducer terminal means coupled to the oscillatory transducer for receiving oscillatory transducer drive signals.

25. The electrode assembly of claim 24 wherein the oscillatory transducer is mounted within the carrier.

26. The electrode assembly of claim 24 wherein the first sensory electrode has greater surface area than the motor electrodes.

27. The electrode assembly of claim 24 wherein the second sensory electrode is positioned adjacent the distal end of the carrier.

28. The invention of claim 24 and further including a controller comprising:
   motor stimulation signal generation and control means coupled to the motor electrode terminal means for producing the motor receptor electrical stimulation signals;
   sensory stimulation signal generation and control means coupled to the sensory stimulation terminal means for producing the sensory receptor electrical stimulation signals; and
   oscillatory drive signal generation and control means coupled to the oscillatory transducer terminal means for producing the oscillatory transducer drive signals.

29. The invention of claim 28 and further including phase control means coupled to the motor stimulation signal generation and control means, to the sensory stimulation signal generation and control means, and to the oscillatory drive signal generation and control means, for controlling a phase relationship between the motor receptor stimulation signals, the sensory receptor electrical stimulation signals, and the oscillatory transducer drive signals.

* * * * *